United States Patent [19]

Weiss et al.

[11] Patent Number: 4,548,903
[45] Date of Patent: Oct. 22, 1985

[54] METHOD TO REVEAL MICROSTRUCTURES IN SINGLE PHASE ALLOYS

[75] Inventors: Isaac Weiss, Dayton; Francis H. Froes, Xenia; Daniel Eylon, Dayton, all of Ohio

[73] Assignee: The United States of America as represented by the Secretary of the Air Force, Washington, D.C.

[21] Appl. No.: 595,153

[22] Filed: Mar. 30, 1984

[51] Int. Cl.⁴ ..................... G01N 21/88; G01N 33/20
[52] U.S. Cl. .......................................... 436/5; 73/104; 75/0.5 R; 156/664; 356/36; 436/73; 436/164
[58] Field of Search ............... 156/664, 645, 665, 651; 75/0.5 R; 436/5, 73, 164; 73/7, 87, 863, 432 R, 432 Z, 104; 356/36; 252/79.3

[56] References Cited

U.S. PATENT DOCUMENTS

| | | | |
|---|---|---|---|
| 3,844,859 | 10/1974 | Roni | 156/664 |
| 3,846,188 | 11/1974 | Werkema | 156/664 |
| 4,001,052 | 1/1977 | Nakazato et al. | 148/12 C |
| 4,076,575 | 2/1978 | Chang | 156/656 |
| 4,220,706 | 9/1980 | Spak | 156/665 |
| 4,310,381 | 1/1982 | DeCristofaro | 148/121 |

OTHER PUBLICATIONS

Eylon, "The Microscope", vol. 23, 3rd Quarter, 1975, pp. 133-137.
Voort, "Metallography Principles & Practice", 1984, McGraw Hill Book Co., N.Y., pp. 185-186.
F. H. Froes, J. M. Capenos and C. F. Yoltan, "Decoration of Plastically Strained Regions in Metallic Systems", Metallography, 9, 1976, pp. 535-537.
E. D. Hondros and A. J. W. Moore, "Thermal Etching of Silver Surfaces Parallel to [110] Planes", Acta. Met., 7, 1959, pp. 521-523.
W. B. Morrison, "Recrystallization of a Low-Carbon Steel in the Austenite Range", Draft of Paper Intended for Publication in JISI, Aug. 1971.

*Primary Examiner*—Arnold Turk
*Attorney, Agent, or Firm*—Donald J. Singer; Charles E. Bricker

[57] ABSTRACT

A method for revealing the microstructure of metal alloys which comprises the steps of polishing the sample, chemically etching the polished metal surface, thermally etching the chemically etched surface and quenching the thermally etched sample. This method allows observation of deformed and recrystallized grains on the same polished surface and provides the opportunity to correlate recrystallized grains to their nucleation sites.

6 Claims, 4 Drawing Figures

METHOD TO REVEAL MICROSTRUCTURES IN SINGLE PHASE ALLOYS

RIGHTS OF THE GOVERNMENT

The invention described herein may be manufactured and used by or for the Government of the United States for all governmental purposes without the payment of any royalty.

BACKGROUND OF THE INVENTION

The present invention relates to metal alloys, and in particular, to a method for revealing deformed and recrystallized structures in single phase alloys.

Metallographic techniques are widely used in research and in industry. Typical uses include investigation of the phase constitution of metallic systems, the microstructure of metals, phase transformations, plastic deformation mechanisms, production heat treatment control and the analysis of the causes of service failures of metallic objects.

The selection and preparation of representative samples for examination is essential. Typically, a specimen is first ground and polished using decreasing grit sizes. These operations render the specimen surface scratch-free and mirrorlike by means of the progressive removal of surface irregularities. Alternatively, the specimen may be electrolytically polished by controlled anodic dissolution.

Polished specimens reveal only a few structural features, such as inclusions, microcracks and microporosity. Etching with an appropriate etchant is necessary to bring out the microstructures. Mechanically polished specimens have a thin surface layer of distorted metal; etching removes the distorted layer.

Etchants include acids, bases and complex substances, generally in dilute solution in water, alcohol, or glycerin. Most reagents act by dissolution, but a few act by selective deposition of reaction products. In a single-phase alloy, etching attacks different parts of the structure selectively. Grain-boundary regions dissolve in preference to the body of the grains and the resulting grooves appear as a dark network. In multiphase alloys the phases are attacked selectively.

Etching by heating the sample in a high vacuum or an oxidizing atmosphere has also proven useful. Thermal etching produces a groove in the metal surface where it is intersected by a grain boundary. Selective evaporation along crystallographic steps is also evident.

We have discovered that chemical and thermal etching may be successively combined to provide a new analytical tool.

Accordingly, it is an object of the present invention to provide a novel method for revealing the microstructure of metal alloys.

Other objects, aspects and advantages of the present invention will be apparent to those skilled in the art from a reading of the following description of the invention.

DESCRIPTION OF THE INVENTION

In accordance with the present invention there is provided an improved method for revealing the microstructure of metal alloys, which comprises the steps of polishing the surface of a metal sample, chemically etching the polished metal surface, thermally etching the previously chemically etched surface and quenching the thermally etched sample.

The following example illustrates the invention:

EXAMPLE

Specimens (20mm×40mm×5mm) having a nominal composition of Ti—10V—2Fe—3Al were deformed 35% at 1150° C. The deformed specimens were polished using 3 micron diamond paste and 0.05 micron alumina to produce a mirror finish surface. The polished samples were etched in a solution containing 60 ml water, 40 ml NH3 (71%) and 10 ml HF (50%) for 30 minutes at room temperature. The deformed and macro etched samples were then annealed for 2 hours at temperatures above 925° C. (1700° F.) under a dynamic vacuum of $10^{-6}$ torr followed by oil quenching under vacuum.

Figure 1:
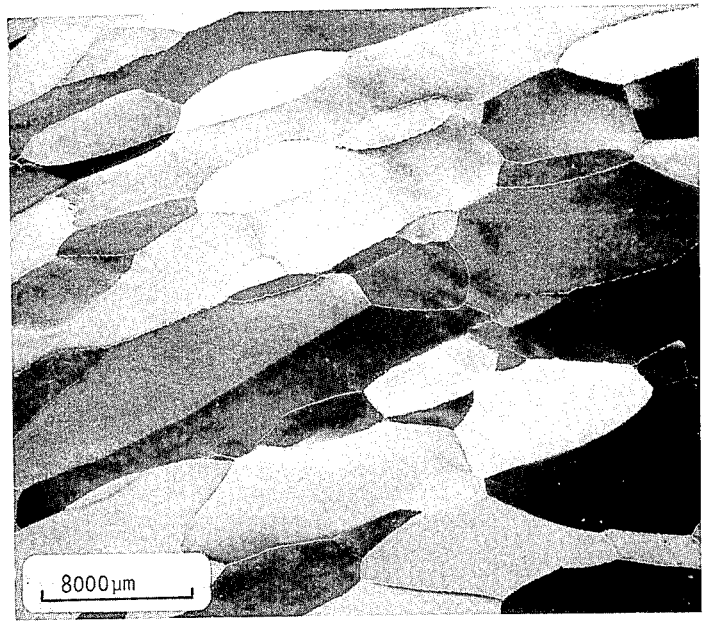
FIG. 1 is a 3× photomicrograph of a specimen illustrating the microstructure obtained following deep chemical etching.

Referring now to the drawings, FIG. 1 illustrates the deformed microstructure following deep chemical etching. Large elongated grains having different orientations may be seen. Most of the grain boundaries are serrated as a result of the deformation applied at 1150° C. The lightly etched grain boundaries are assumed to be of lower orientation mismatch and do not exhibit a pronounced serration. Some fine recrystallized grains can also be observed along the deformed grain boundaries. These probably were nucleated immediately after deformation during the cooling.

Figure 2:
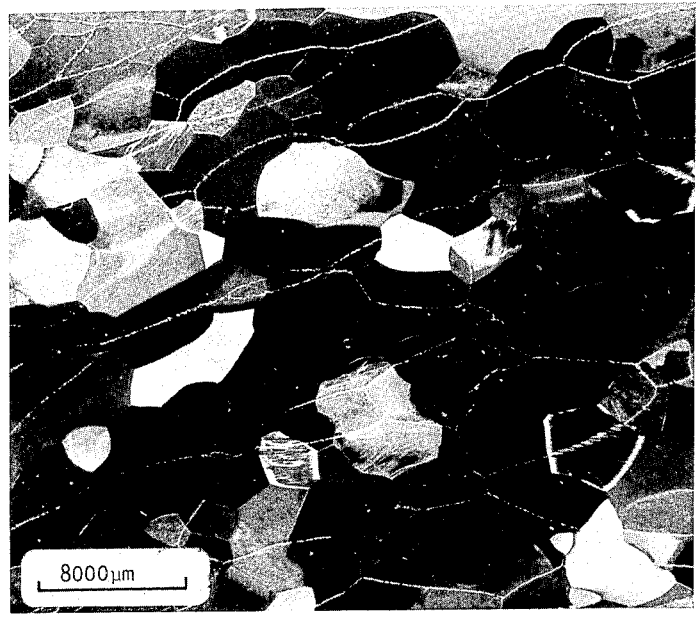
FIG. 2 is a 3× photomicrograph of a specimen illustrating the microstructure obtained following deep chemical etching and subsequent thermal etching.

The subsequent vaccum annealing above 925° C. causes simultaneous recrystallization and thermal etching to take place on the polished and macroetched surface. The rate of thermal etching is dependent upon grain orientation, and is, therefore, different for each grain. As seen in FIG. 2, the resulting thermally etched surface reveals a microstructure after quenching in which recrystallized grains are superimposed onto the image of most of the original deformed grain boundaries. The white boundaries observed in FIG. 2 are "ghost" boundaries. Comparison of FIG. 2 with FIG. 1 reveals that the "ghost" boundaries of FIG. 2 represent the prior deformed grain boundaries of FIG. 1, these boundaries having been retained as a result of the deep chemical grooving during the chemical etching. The "ghost" boundaries seen in FIG. 2 do not migrate with the grain boundaries as a result of recrystallization during annealing. The faint grooving observable between some grains is probably the result of a low degree of misorientation. Some of the deformed grain boundaries may be observed to be missing from FIG. 2 when compared to FIG. 1, probably as a result of misoriented boundaries.

Figure 3:
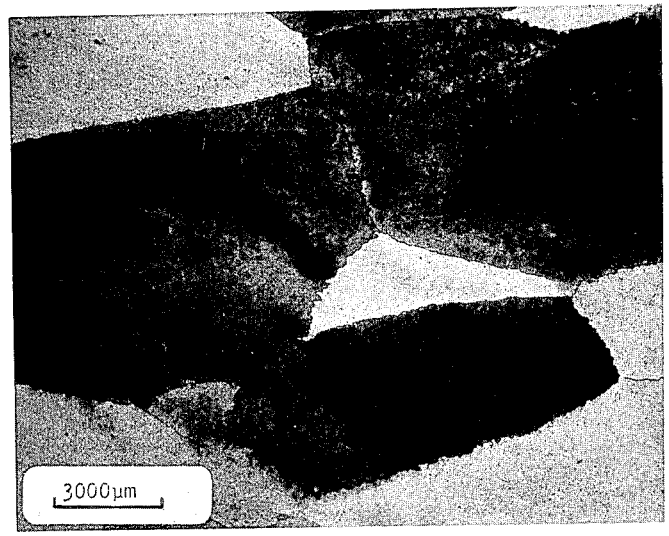
FIG. 3 is a 6× photomicrograph of a specimen illustrating the microstructure obtained following deep chemical etching and subsequent thermal etching.

The ability to observe deformed and recrystallized grains on the same polished surface provides the opportunity to correlate the recrystallized grains to their nucleation sites in a way never done before. FIG. 3 is a 6× magnification of the grain structure after 35% deformation at 1150° C., and prior to chemical and thermal etching. The grain boundaries exhibit localized bulging. These grain boundary segments have a high degree of misorientation and are highly mobile. Some fine recrystallized grains are also present in triple points. The grains shown are a result of dynamic or fast static recrystallization.

Figure 4:
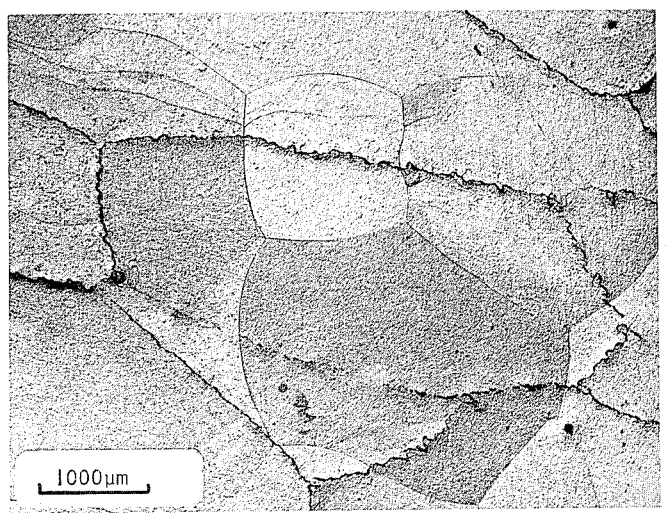
FIG. 4 is an 18× photomicrograph of a specimen illustrating the microstructure obtained following deep chemical etching and subsequent thermal etching.

FIG. 4 illustrates a sample at a greater magnification (18×) following chemical etching and vacuum annealing at 1350° C. for 2 hours followed by oil quenching. From FIG. 4 it appears that grain boundary segments and triple points act as nucleation sites for the recrystallized grains.

The method of this invention is applicable to any metal alloy, particularly, metal alloys normally characterized as being of the single phase variety. Examples of suitable alloys include α-titanium alloys, β-titanium alloys, ferrous alloys, aluminum alloys and the like.

The specimen is first polished to a mirror finish using materials and procedures known in the art. The etchant employed in the chemical macro etching step may be any etchant generally used for etching metal samples for microscopic observation. Suitable etchants include the buffered HF solution disclosed above for Ti alloys, HF solution for Al alloys, picric acid solution for ferrous alloys, and the like. The conditions for chemical etching including etchant solution strength, time, temperature, and the like, must be determined by the user.

The conditions for thermal etching of the specimen are dependent upon the particular alloy employed as well as the results desired. In general, the thermal etching step is carried out at a temperature in the approximate range of 0.6 to 0.8 times the melt temperature of the alloy, in degrees-K., under vacuum conditions of $10^{-3}$ torr or less, preferable less than about $10^{-5}$ torr, for a period of about 0.25 to about 3 hours. Immediately following the thermal etching step, the specimen is quenched in a suitable quenching fluid, such as an oil, to preserve the high temperature structure of the specimen. Preferably, quenching is carried out under vacuum, inside the chamber used for thermal etching. It is, however, within the scope of the present invention to allow the specimen to cool from the thermal etching temperature to a lower temperature prior to quenching the specimen.

Various modifications may be made to the present invention without departing from the spirit of the invention or the scope of the appended claims.

We claim:

1. A method for revealing the microstructure of metal alloys to permit the observation of both deformed and recrystallized grains on the same metal surface which comprises the steps of polishing a surface of a metal sample, chemically etching the polished metal surface, thermally etching the resulting chemically etched surface and quenching the thermally etched sample.

2. The method of claim 1 wherein said metal alloy is a single phase metal alloy.

3. The method of claim 1 wherein said thermal etching step is carried out at a temperature in the approximate range of 0.6 to 0.8 times the melt temperature of said alloy under a vacuum of not greater than about $10^{-3}$ torr for a period of about 0.25 to about 3 hours.

4. The method of claim 3 wherein said metal alloy is a titanium alloy and wherein said chemical etching step comprises etching said alloy in a buffered HF solution.

5. The method of claim 3 wherein said metal alloy is an aluminum alloy and wherein said chemical etching step comprises etching said alloy in an HF solution.

6. The method of claim 3 wherein said metal alloy is a ferrous alloy and wherein said chemical etching step comprises etching said alloy in a picric acid solution.

* * * * *